United States Patent
Krenzer

[11] 3,932,410
[45] Jan. 13, 1976

[54] 1-THIADIAZOLYL-6-ALKOXYTETRAHY-DROPYRIMIDINONES

[75] Inventor: John Krenzer, Oak Park, Ill.

[73] Assignee: Velsicol Chemical Corporation, Chicago, Ill.

[22] Filed: Nov. 1, 1974

[21] Appl. No.: 519,896

[52] U.S. Cl. .............................. 260/256.5 R; 71/90
[51] Int. Cl.² ....................................... C07D 239/00
[58] Field of Search ............................. 260/256.5 R

[56] References Cited
UNITED STATES PATENTS

| | | | |
|---|---|---|---|
| 3,299,069 | 1/1967 | Schmidt et al. | 260/256.5 R |
| 3,627,777 | 12/1971 | Schmidt et al. | 260/256.5 R |
| 3,829,422 | 8/1974 | Hardtmann et al. | 260/256.5 R |

*Primary Examiner*—Leonard Schenkman
*Attorney, Agent, or Firm*—Robert J. Schwarz; Dietmar H. Olesch

[57] ABSTRACT

Disclosed are new compounds of the formula

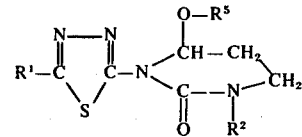

wherein $R^1$ is selected from the group consisting of alkyl, alkenyl, haloalkyl, alkoxy, alkylthio, alkylsulfonyl and alkylsulfinyl; $R^2$ is selected from the group consisting of alkyl, alkenyl, haloalkyl and

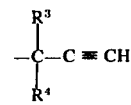

wherein $R^3$ and $R^4$ are each selected from the group consisting of hydrogen and alkyl; and $R^5$ is alkyl. The subject compounds are useful as herbicides.

8 Claims, No Drawings

1-THIADIAZOLYL-6-ALKOXYTETRAHY-DROPYRIMIDINONES

This invention relates to new compositions of matter and more specifically relates to new chemical compounds of the formula

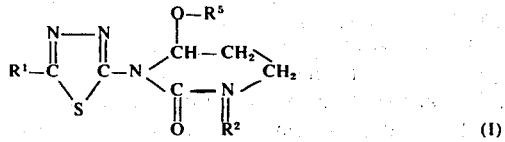

(I)

wherein $R^1$ is selected from the group consisting of alkyl, alkenyl, haloalkyl, alkoxy, alkylthio, alkylsulfonyl and alkylsulfinyl; $R^2$ is selected from the group consisting of alkyl, alkenyl, haloalkyl and

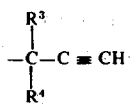

wherein $R^3$ and $R^4$ are each selected from the group consisting of hydrogen and alkyl; and $R^5$ is alkyl.

In a preferred embodiment of the present invention $R^1$ is selected from the group consisting of lower alkyl, lower alkenyl, lower chloroalkyl, lower bromoalkyl, trifluoromethyl, lower alkoxy, lower alkylthio, lower alkylsulfonyl and lower alkylsulfinyl; $R^2$ is selected from the group consisting of lower alkyl, lower alkenyl, lower chloroalkyl, lower bormoalkyl and

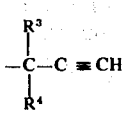

wherein $R^3$ and $R^4$ are each selected from the group consisting of hydrogen and lower alkyl; and $R^5$ is lower alkyl.

The term lower as used herein designates a straight or branched carbon chain of up to six carbon atoms.

The compounds of the present invention are unexpectedly useful as herbicides.

The compounds of this invention can be readily prepared by reacting a compound of the formula

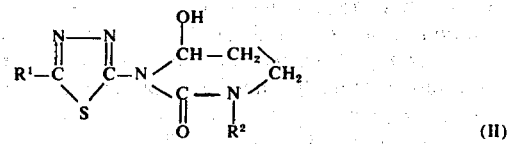

(II)

wherein $R^1$ and $R^2$ are as heretofore described, with an alcohol of the formula $$R^5OH \qquad (III)$$

wherein $R^5$ is as heretofore described. This reaction can be effected by combining the compound of formula II with an excess molar amount of the alcohol of formula III in the presence of a catalytic amount of toluenesulfonic acid and heating the reaction mixture at a temperature of from about 50°C to about the reflux temperature of the mixture for a period of from about 6 to about 24 hours. After this time the reaction mixture can be stripped of excess alcohol under reduced pressure to yield the desired product as the residue. This product can then be used as such or can be further purified by conventional techniques such as recrystallization and the like.

The compounds of formula II can be prepared by heating a compound of the formula

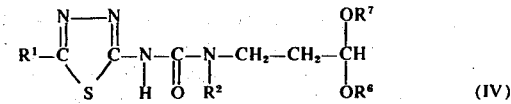

(IV)

wherein $R^1$ and $R^2$ are as heretofore described and $R^6$ and $R^7$ are methyl or ethyl, in a dilute, aqueous, acidic reaction medium for a period of about 10 to about 60 minutes. Temperatures of from about 70°C to the reflux temperature of the reaction mixture can be utilized. The reaction medium can comprise a dilute aqueous inorganic acid such as hydrochloric acid at a concentration of from about 0.5 to about 5 percent. Upon completion of the reaction the desired product can be recovered as a precipitate by cooling the reaction mixture. This product can be used as such or can be further purified by conventional means such as recrystallization and the like.

The compounds of formula IV can be prepared by reacting a molar amount of an isocyanate dimer of the formula

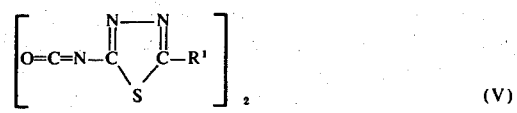

(V)

wherein $R^1$ is as heretofore described, with about two molar amounts of an acetal of the formula

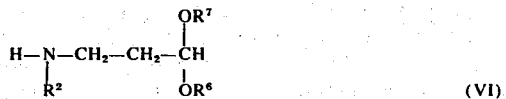

(VI)

wherein $R^2$, $R^6$ and $R^7$ are as heretofore described. This reaction can be effected by heating a mixture of the isocyanate dimer and the acetal in an inert organic reaction medium such as benzene at the reflux temperature of the reaction mixture. Heating at reflux can be continued for a period of from about 2 to about 30 minutes to ensure completion of the reaction. After this time the desired product can be recovered upon evaporation of the reaction medium and can be used as such or can be further purified by standard techniques in the art.

The isocyanate dimer of formula V can be prepared by reacting a thiadiazole of the formula

(VII)

wherein $R^1$ is as heretofore described, with phosgene. This reaction can be effected by adding a slurry or solution of the thiadiazole, in a suitable organic solvent such as ethyl acetate, to a saturated solution of phosgene in an organic solvent such as ethyl acetate. The resulting mixture can be stirred at ambient temperatures for a period of from about 4 to about 24 hours. The reaction mixture can then be purged with nitrogen gas to remove unreacted phosgene. The desired product can then be recovered by filtration if formed as a precipitate or upon evaporation of the organic solvent used if soluble therein. This product can be used as such or can be further purified if desired.

Exemplary thiadiazoles of formula VII useful for preparing the compounds of the present invention are 5-methyl-2-amino-1,3,4-thiadiazole, 5-ethyl-2-amino-1,3,4-thiadiazole, 5-propyl-2-amino-1,3,4-thiadiazole, 5-allyl-2-amino-1,3,4-thiadiazole, 5-pent-3-enyl-2-amino-1,3,4-thiadiazole, 5-chloromethyl-2-amino-1,3,4-thiadiazole, 5-β-chloroethyl-2-amino-1,3,4-thiadiazole, 5-γ-chloropropyl-2-amino-1,3,4-thiadiazole, 5-trichloromethyl-2-amino-1,3,4-thiadiazole, 5-methoxy-2-amino-1,3,4-thiadiazole, 5-ethoxy-2-amino-1,3,4-thiadiazole, 5-propoxy-2-amino-1,3,4-thiadiazole, 5-butyloxy-2-amino-1,3,4-thiadiazole, 5-hexyloxy-2-amino-1,3,4-thiadiazole, 5-methylthio-2-amino-1,3,4-thiadiazole, 5-ethylthio-2-amino-1,3,4-thiadiazole, 5-propylthio-2-amino-1,3,4-thiadiazole, 5-butylthio-2-amino-1,3,4-thiadiazole, 5-methylsulfonyl-2-amino-1,3,4-thiadiazole, 5-ethylsulfonyl-2-amino-1,3,4-thiadiazole, 5-butylsulfonyl-2-amino-1,3,4-thiadiazole, 5-methylsulfinyl-2-amino-1,3,4-thiadiazole, 5-ethylsulfinyl-2-amino-1,3,4-thiadiazole, 5-propylsulfinyl-2-amino-1,3,4-thiadiazole, 5-t-butyl-2-amino-1,3,4-thiadiazole, 5-trifluoromethyl-2-amino- 1,3,4-thiadiazole and the like.

The acetal of formula VI when not readily available can be prepared by reacting an amine of the formula

(VIII)

wherein $R^2$ is as heretofore described with the dimethyl or diethyl acetal of β-bromopropionaldehyde. This reaction can be effected by combining from about 1 to about 2 molar amounts of the amine of formula VIII with one molar amount of the acetal of β-bromopropionaldehyde in about equimolar proportions in an inert organic reaction medium such as methanol. The reaction mixture can then be heated at reflux for a period of from about 4 to about 8 hours. After this time the reaction mixture can be cooled to room temperature and an alkali metal hydroxide or carbonate can be added in an amount sufficient to neutralize the reaction mixture. Stirring can be continued at room temperature for a period of up to about 24 hours to ensure completion of the reaction. After this time the reaction mixture can be filtered and the filtrate distilled under reduced pressure to yield the desired product.

Exemplary compounds of formula VIII are methylamine, ethylamine, propylamine, isopropylamine, n-butylamine, t-butylamine, pentylamine, hexylamine, allylamine, propargylamine, 2-butenylamine, 3-butenylamine, 3-pentenylamine, 4-pentenylamine, 5-hexenylamine, 1-methyl-2-propynylamine, 1,1-dimethyl-2-propynylamine, 1-ethyl-2-propynylamine, 1,1-diethyl-2-propynylamine, 1-propyl-2-propynylamine, 1,1-dipropyl-2-propynylamine, 1-chloroallylamine, 1-bromoallylamine, 4-chloro-2-butenylamine, 6-chloro-4-hexenylamine and the like.

Exemplary useful alcohols of formula III are methanol, ethanol, propanol, isopropanol, butanol, sec-butanol, t-butanol, pentanol, hexanol and the like.

The manner in which the compounds of the present invention can be prepared is more specifically illustrated in the following examples.

EXAMPLE 1

Preparation of 5-Methyl-1,3,4-thiadiazol-2-yl Isocyanate Dimer

A saturated solution of phosgene in ethyl acetate (100 ml) is charged into a glass reaction vessel equipped with a mechanical stirrer. A slurry of 5-methyl-2-amino-1,3,4-thiadiazole (40 grams) in ethyl acetate (300 ml) is added to the reaction vessel and the resulting mixture is stirred for a period of about 16 hours, resulting in the formation of a precipitate. The reaction mixture is then purged with nitrogen gas to remove unreacted phosgene. The purged mixture is then filtered to recover the precipitate. The precipitate is then recrystallized to yield the desired product 5-methyl-1,3,4-thiadiazol-2-yl isocyanate dimer.

EXAMPLE 2

Preparation of the Dimethyl Acetal of 3-Methylaminopropionaldehyde

Methylamine (1.0 mole), the dimethyl acetal of 3-bromopropionaldehyde (0.5 mole) and methanol (100 ml) are charged into a glass reaction vessel equipped with a mechanical stirrer, thermometer and reflux condenser. The reaction mixture is heated at reflux, with stirring, for a period of about 4 hours. After this time the reaction mixture is cooled to room temperature and sodium hydroxide (20 grams) is added. The reaction mixture is then stirred for an additional period of about 8 hours. The reaction mixture is then filtered and the filtrate is distilled under reduced pressure to yield the desired product the dimethyl acetal of 3-methylaminopropionaldehyde.

EXAMPLE 3

Preparation of the Dimethyl Acetal of 3-[1-Methyl-3-(5-methyl-1,3,4-thiadiazol-2-yl)ureido]propionaldehyde A mixture of 5-methyl-1,3,4-thiadiazol-2-yl isocyanate dimer (0.05 mole), the dimethyl acetal of 3-methylaminopropionaldehyde (0.1 mole) and benzene (60 ml) are charged into a glass reaction vessel equipped with a mechanical stirrer and reflux condenser. The reaction mixture is heated at reflux for a period of about 15 minutes. After this time the mixture is stripped of benzene under reduced pressure to yield a solid product as the residue. The residue is then recrystallized to yield the desired product the dimethyl acetal of 3-[1-methyl-3-(5-methyl-1,3,4-thiadiazol-2-yl)ureido]propionaldehyde.

EXAMPLE 4

Preparation of Tetrahydro-1-(5-methyl-1,3,4-thiadiazol-2-yl)-3-methyl-6-hydroxy-2(1H)-pyrimidinone The dimethyl acetal of 3-[1-methyl-3-(5-methyl-1,3,4-thiadiazol-2-yl)ureido]propionaldehyde (15 grams), water (400 ml) and hydrochloric acid (4 ml) are charged into a glass reaction vessel equipped with a mechanical stirrer, thermometer and reflux condenser. The reaction mixture is heated at reflux for a period of about 15 minutes. The reaction mixture is then filtered while hot and the filtrate is cooled to form a precipitate. The precipitate is recovered by filtration, is dried and is recrystallized to yield the desired product tetrahydro-1-(5-methyl-1,3,4-thiadiazol-2-yl)-3-methyl-6-hydroxy-2(1H)-pyrimidinone.

EXAMPLE 5

Preparation of Tetrahydro-1-(5-methyl-1,3,4-thiadiazol-2-yl)-3-methyl-6-methoxy-2(1H)-pyrimidinone Tetrahydro-1-(5-methyl-1,3,4-thiadiazol-2-yl)-3-methyl-6-hydroxy-2(1H)-pyrimidinone (7 grams), methyl alcohol (50 ml) and toluenesulfonic acid (0.2 grams) are charged into a glass reaction vessel equipped with a mechanical stirrer, thermometer and reflux condenser. The reaction mixture is then heated at reflux for a period of about 24 hours. After this time the mixture is stripped of unreacted alcohol under reduced pressure to yield a solid product. This product is then recrystallized to yield the desired product tetrahydro-1-(5-methyl-1,3,4-thiadiazol-2-yl)-3-methyl-6-methoxy-2(1H)-pyrimidinone.

EXAMPLE 6

Preparation of 5-Methoxy-1,3,4-thiadiazol-2-yl Isocyanate Dimer

A saturated solution of phosgene in ethyl acetate (100 ml) is charged into a glass reaction vessel equipped with a mechanical stirrer. A slurry of 5-methoxy-2-amino-1,3,4-thiadiazole (40 grams) in ethyl acetate (300 ml) is added to the reaction vessel and the resulting mixture is stirred for a period of about 16 hours, resulting in the formation of a precipitate. The reaction mixture is then purged with nitrogen gas to remove unreacted phosgene. The purged mixture is then filtered to recover the precipitate. The precipitate is then recrystallized to yield the desired product 5-methoxy-1,3,4-thiadiazol-2-yl isocyanate dimer.

EXAMPLE 7

Preparation of the Dimethyl Acetal of 3-Ethylaminopropionaldehyde

Ethylamine (2.0 mole), the dimethyl acetal of 3-bromopropionaldehyde (1.0 mole) and methanol (100 ml) are charged into a glass reaction vessel equipped with a mechanical stirrer, thermometer and reflux condenser. The reaction mixture is heated at reflux, with stirring, for a period of about 5 hours. After this time the reaction mixture is cooled to room temperature and sodium hydroxide (20 grams) is added. The reaction mixture is then stirred for an additional period of about 12 hours. The reaction mixture is then filtered and the filtrate is distilled under reduced pressure to yield the desired product the dimethyl acetal of 3-ethylaminopropionaldehyde.

EXAMPLE 8

Preparation of the Dimethyl Acetal of 3-[1-(Ethyl-3-(5-methoxy-1,3,4-thiadiazol-2-yl)ureido]propionaldehyde A mixture of 5-methoxy-1,3,4-thiadiazol-2-yl isocyanate dimer (0.05 mole), the dimethyl acetal of 3-ethylaminopropionaldehyde (0.1 mole) and benzene (60 ml) are charged into a glass reaction vessel equipped with a mechanical stirrer and reflux condenser. The reaction mixture is heated at reflux for a period of about 15 minutes. After this time the mixture is stripped of benzene under reduced pressure to yield a solid product as the residue. The residue is then recrystallized to yield the desired product the dimethyl acetal of 3-[1-ethyl-3-(5-methoxy-1,3,4-thiadiazol-2-yl)ureido]propionaldehyde.

EXAMPLE 9

Preparation of Tetrahydro-1-(5-methoxy-1,3,4-thiadiazol-2-yl)-3-ethyl-6-hydroxy-2(1H)-pyrimidinone The dimethyl acetal of 3-[1-ethyl-3-(5-methoxy-1,3,4-thiadiazol-2-yl)ureido]propionaldehyde (15 grams), water (400 ml) and hydrochloric acid (4 ml) are charged into a glass reaction vessel equipped with a mechanical stirrer, thermometer and reflux condenser. The reaction mixture is heated at reflux for a period of about 15 minutes. The reaction mixture is then filtered while hot and the filtrate is cooled to form a precipitate. The precipitate is recovered by filtration, is dried and is recrystallized to yield the desired product tetrahydro-1-(5-methoxy-1,3,4-thiadiazol-2-yl)-3-ethyl-6-hydroxy-2(1H)-pyrimidinone.

EXAMPLE 10

Preparation of Tetrahydro-1-(5-methoxy-1,3,4-thiadiazol-2-yl)-3-ethyl-6-ethoxy-2(1H)-pyrimidinone Tetrahydro-1-(5-methoxy-1,3,4-thiadiazol-2-yl)-3-ethyl-6-hydroxy-2(1H)-pyrimidinone (7 grams), ethyl alcohol (50 ml) and toluenesulfonic acid (0.2 grams) are charged into a glass reaction vessel equipped with a mechanical stirrer, thermometer and reflux condenser. The reaction mixture is then heated at reflux for a period of about 24 hours. After this time the mixture is stripped of unreacted alcohol under reduced pressure to yield a solid product. This product is then recrystallized to yield the desired product tetrahydro-1-(5-methoxy-1,3,4-thiadiazol-2-yl)-3-ethyl-6-ethoxy-2(1H)-pyrimidinone.

EXAMPLE 11

Preparation of 5-Methylthio-1,3,4-thiadiazol-2-yl Isocyanate Dimer

A saturated solution of phosgene in ethyl acetate (100 ml) is charged into a glass reaction vessel equipped with a mechanical stirrer. A slurry of 5-methylthio-2-amino-1,3,4-thiadiazole (45 grams) in ethyl acetate (300 ml) is added to the reaction vessel and the resulting mixture is stirred for a period of about 16 hours, resulting in the formation of a precipitate. The reaction mixture is then purged with nitrogen gas to remove unreacted phosgene. The purged mixture is then filtered to recover the precipitate. The precipitate is then recrystallized to yield the desired product 5-methylthio-1,3,4-thiadiazol-2-yl isocyanate dimer.

EXAMPLE 12

Preparation of the Dimethyl Acetal of 3-Propylaminopropionaldehyde

Propylamine (2.0 mole), the dimethyl acetal of 3-bromopropionaldehyde (1.0 mole) and methanol (100 ml) are charged into a glass reaction vessel equipped with a mechanical stirrer, thermometer and reflux condenser. The reaction mixture is heated at reflux, with stirring, for a period of about 3 hours. After this time the reaction mixture is cooled to room temperature and sodium hydroxide (20 grams) is added. The reaction mixture is then stirred for an additional period of about 6 hours. The reaction mixture is then filtered and the filtrate is distilled under reduced pressure to yield the desired product the dimethyl acetal of 3-propylaminopropionaldehyde.

EXAMPLE 13

Preparation of the Dimethyl Acetal of 3-[1-Propyl-3-(5-methylthio-1,3,4-thiadiazol-2-yl)ureido]propionaldehyde A mixture of 5-methylthio-1,3,4-thiadiazol-2-yl isocyanate dimer (0.05 mole), the dimethyl acetal of 3-propylpropionaldehyde (0.1 mole) and benzene (60 ml) are charged into a glass reaction vessel equipped with a mechanical stirrer and reflux condenser. The reaction mixture is heated at reflux for a period of about 15 minutes. After this time the mixture is stripped of benzene under reduced pressure to yield a solid product as the residue. The residue is then recrystallized to yield the desired product the dimethyl acetal of 3-[1-propyl-3-(5-methylthio-1,3,4-thiadiazol-2-yl)ureido]propionaldehyde.

EXAMPLE 14

Preparation of Tetrahydro-1-(5-methylthio-1,3,4-thiadiazol-2-yl)-3-propyl-6-hydroxy-2(1H)-pyrimidinone The dimethyl acetal of 3-[1-propyl-3-(5-methylthio-1,3,4-thiadiazol-2-yl)ureido]propionaldehyde (15 grams), water (400 ml) and hydrochloric acid (4 ml) are charged into a glass reaction vessel equipped with a mechanical stirrer, thermometer and reflux condenser. The reaction mixture is heated at reflux for a period of about 15 minutes. The reaction mixture is then filtered while hot and the filtrate is cooled to form a precipitate. The precipitate is recovered by filtration, is dried and is recrystallized to yield the desired product tetrahydro-1-(5-methylthio-1,3,4-thiadiazol-2-yl)-3-propyl-6-hydroxy-2(1H)-pyrimidinone.

EXAMPLE 15

Preparation of Tetrahydro-1-(5-methylthio-1,3,4-thiadiazol-2-yl)-3-propyl-6-propoxy-2(1H)-pyrimidinone Tetrahydro-1-(5-methylthio-1,3,4-thiadiazol-2-yl)-3-propyl-6-hydroxy-2(1H)-pyrimidinone (7 grams), propyl alcohol (50 ml) and toluenesulfonic acid (0.2 grams) are charged into a glass reaction vessel equipped with a mechanical stirrer, thermometer and reflux condenser. The reaction mixture is then heated at reflux for a period of about 24 hours. After this time the mixture is stripped of unreacted alcohol under reduced pressure to yield a solid product. This product is then recrystallized to yield the desired product tetrahydro-1-(5-methylthio-1,3,4-thiadiazol-2-yl)-3-propyl-6-propoxy-2(1H)-pyrimidinone.

EXAMPLE 16

Preparation of 5-Methylsulfonyl-1,3,4-thiadiazol-2-yl Isocyanate Dimer

A saturated solution of phosgene in ethyl acetate (100 ml) is charged into a glass reaction vessel equipped with a mechanical stirrer. A slurry of 5-methylsulfonyl-2-amino-1,3,4-thiadiazole (50 grams) in ethyl acetate (300 ml) is added to the reaction vessel and the resulting mixture is stirred for a period of about 16 hours, resulting in the formation of a precipitate. The reaction mixture is then purged with nitrogen gas to remove unreacted phosgene. The purged mixture is then filtered to recover the precipitate. The precipitate is then recrystallized to yield the desired product 5-methylsulfonyl-1,3,4-thiadiazol-2-yl isocyanate dimer.

EXAMPLE 17

Preparation of the Dimethyl Acetal of 3-Allylaminopropionaldehyde

Allylamine (1.0 mole), the dimethyl acetal of 3-bromopropionaldehyde (0.5 mole) and methanol (100 ml) are charged into a glass reaction vessel equipped with a mechanical stirrer, thermometer and reflux condenser. The reaction mixture is heated at reflux, with stirring, for a period of about 8 hours. After this time the reaction mixture is cooled to room temperature and sodium hydroxide (20 grams) is added. The reaction mixture is then stirred for an additional period of about 14 hours. The reaction mixture is then filtered and the filtrate is distilled under reduced pressure to yield the desired product the dimethyl acetal of 3-allylaminopropionaldehyde.

EXAMPLE 18

Preparation of the Dimethyl Acetal of 3-[1-Allyl-3-(5-methylsulfonyl-1,3,4-thiadiazol-2-yl)ureido]propionaldehyde A mixture of 5-methylsulfonyl-1,3,4-thiadiazol-2-yl isocyanate dimer (0.05 mole), the dimethyl acetal of 3-allylaminopropionaldehyde (0.1 mole) and benzene (60 ml) are charged into a glass reaction vessel equipped with a mechanical stirrer and reflux condenser. The reaction mixture is heated at reflux for a period of about 15 minutes. After this time the mixture is stripped of benzene under reduced pressure to yield a solid product as the residue. The residue is then recrystallized to yield the desired product the dimethyl acetal of 3-[1-allyl-3-(5-methylsulfonyl-1,3,4-thiadiazol-2-yl)ureido]propionaldehyde.

EXAMPLE 19

Preparation of Tetrahydro-1-(5-methylsulfonyl-1,3,4-thiadiazol-2-yl)-3-allyl-6-hydroxy-2(1H)-pyrimidinone The dimethyl acetal of 3-[1-methyl-3-(5-methyl-sulfonyl-1,3,4-thiadiazol-2-yl)ureido]propionaldehyde (15 grams), water (400 ml) and hydrochloric acid (4 ml) are charged into a glass reaction vessel equipped with a mechanical stirrer, thermometer and reflux condenser. The reaction mixture is heated at reflux for a period of about 15 minutes. The reaction mixture is then filtered while hot and the filtrate is cooled to form a precipitate. The precipitate is recovered by filtration, is dried and is recrystallized to yield the desired product tetrahydro-1-(5-methylsulfonyl-1,3,4-thiadiazol-2-yl)-3-allyl-6-hydroxy-2(1H)-pyrimidinone.

EXAMPLE 20

Preparation of Tetrahydro-1-(5-methylsulfonyl-1,3,4-thiadiazol-2-yl)-3-allyl-6-butoxy-2(1H)-pyrimidinone Tetrahydro-1-(5-methylsulfonyl-1,3,4-thiadiazol-2-yl)-3-allyl-6-hydroxy-2(1H)-pyrimidinone (7 grams), butyl alcohol (50 ml) and toluenesulfonic acid (0.2 grams) are charged into a glass reaction vessel equipped with a mechanical stirrer, thermometer and reflux condenser. The reaction mixture is then heated at reflux for a period of about 24 hours. After this time the mixture is stripped of unreacted alcohol under reduced pressure to yield a solid product. This product is then recrystallized to yield the desired product tetrahydro-1-(5-methylsulfonyl-1,3,4-thiadiazol-2-yl)-3-allyl-6-butoxy-2(1H)-pyrimidinone.

EXAMPLE 21

Preparation of 5-Methylsulfinyl-1,3,4-thiadiazol-2-yl Isocyanate Dimer

A saturated solution of phosgene in ethyl acetate (100 ml) is charged into a glass reaction vessel equipped with a mechanical stirrer. A slurry of 5-methylsulfinyl-2-amino-1,3,4-thiadiazole (50 grams) in ethyl acetate (300 ml) is added to the reaction vessel and the resulting mixture is stirred for a period of about 16 hours, resulting in the formation of a precipitate. The reaction mixture is then purged with nitrogen gas to remove unreacted phosgene. The purged mixture is then filtered to recover the precipitate. The precipitate is then recrystallized to yield the desired product 5-methylsulfinyl-1,3,4-thiadiazol-2-yl isocyanate dimer.

EXAMPLE 22

Preparation of the Dimethyl Acetal of 3-Propargylaminopropionaldehyde

Propargylamine (2.0 mole), the dimethyl acetal of 3-bromopropionaldehyde (1.0 mole) and methanol (100 ml) are charged into a glass reaction vessel equipped with a mechanical stirrer, thermometer and reflux condenser. The reaction mixture is heated at reflux, with stirring, for a period of about 6 hours. After this time the reaction mixture is cooled to room temperature and sodium hydroxide (20 grams) is added. The reaction mixture is then stirred for an additional period of about 18 hours. The reaction mixture is then filtered and the filtrate is distilled under reduced pressure to yield the desired product the dimethyl acetal of 3-propargylaminopropionaldehyde.

EXAMPLE 23

Preparation of the Dimethyl Acetal of 3-[1-Propargyl-3-(5-methylsulfinyl-1,3,4-thiadiazol-2-yl)ureido]propionaldehyde A mixture of 5-methylsulfinyl-1,3,4-thiadiazol-2-yl isocyanate dimer (0.05 mole), the dimethyl acetal of 3-propargylaminopropionaldehyde (0.1 mole) and benzene (60 ml) are charged into a glass reaction vessel equipped with a mechanical stirrer and reflux condenser. The reaction mixture is heated at reflux for a period of about 15 minutes. After this time the mixture is stripped of benzene under reduced pressure to yield a solid product as the residue. The residue is then recrystallized to yield the desired product the dimethyl acetal of 3-[1-propargyl-3-(5-methylsulfinyl-1,3,4-thiadiazol-2-yl)ureido]propionaldehyde.

EXAMPLE 24

Preparation of Tetrahydro-1-(5-methylsulfinyl-1,3,4-thiadiazol-2-yl)-3-propargyl-6-hydroxy-2(1H)-pyrimidinone The dimethyl acetal of 3-[1-propargyl-3-(5-methylsulfinyl-1,3,4-thiadiazol-2-yl)ureido]propionaldehyde (15 grams), water (400 ml) and hydrochloric acid (4 ml) are charged into a glass reaction vessel equipped with a mechanical stirrer, thermometer and reflux condenser. The reaction mixture is heated at reflux for a period of about 15 minutes. The reaction mixture is then filtered while hot and the filtrate is cooled to form a precipitate. The precipitate is recovered by filtration, is dried and is recrystallized to yield the desired product tetrahydro-1-(5-methylsulfinyl-1,3,4-thiadiazol-2-yl)-3-propargyl-6-hydroxy-2(1H)-pyrimidinone.

EXAMPLE 25

Preparation of Tetrahydro-1-(5-methylsulfinyl-1,3,4-thiadiazol-2-yl)-3-propargyl-6-hexyloxy-2(1H)-pyrimidinone Tetrahydro-1-(5-methylsulfinyl-1,3,4-thiadiazol-2-yl)-3-propargyl-6-hydroxy-2(1H)-pyrimidinone (7 grams), hexyl alcohol (50 ml) and toluenesulfonic acid (0.2 grams) are charged into a glass reaction vessel equipped with a mechanical stirrer, thermometer and reflux condenser. The reaction mixture is then heated at reflux for a period of about 24 hours. After this time the mixture is stripped of unreacted alcohol under reduced pressure to yield a solid product. This product is then recrystallized to yield the desired product tetrahydro-1-(5-methylsulfinyl-1,3,4-thiadiazol-2-yl)- 3-propargyl-6-hexyloxy-2(1H)-pyrimidinone.

EXAMPLE 26

Preparation of 5-Trifluoromethyl-1,3,4-thiadiazol-2-yl Isocyanate Dimer

A saturated solution of phosgene in ethyl acetate (100 ml) was charged into a glass reaction vessel equipped with a mechanical stirrer. A slurry of 5-trifluoromethyl-2-amino-1,3,4-thiadiazole (45 grams) in ethyl acetate (300 ml) was added to the reaction vessel and the resulting mixture was stirred for a period of about 16 hours resulting in the formation of a precipitate. The reaction mixture was then purged with nitrogen gas to remove unreacted phosgene. The purged mixture was filtered to recover 48 grams of a white solid. This solid was recrystallized from dimethyl formamide to yield the desired product 5-trifluoromethyl-1,3,4-thiadiazol-2-yl isocyanate dimer.

EXAMPLE 27

Preparation of the Dimethyl Acetal of 3-[1-Methyl-3-(5-trifluoromethyl-1,3,4-thiadiazol-2-yl)ureido]propionaldehyde A mixture of 5-trifluoromethyl-1,3,4-thiadiazol-2-yl isocyanate dimer (9.5 grams), the dimethyl acetal of 3-methylaminopropionaldehyde (5.8 grams) and benzene (60 ml) are charged into a glass reaction vessel equipped with a mechanical stirrer and reflux condenser. The reaction mixture is heated at reflux for a period of about 15 minutes. After this time the mixture is stripped of benzene under reduced pressure to yield a solid product as the residue. This product is recrystallized to yield the desired product the dimethyl acetal of 3-[1-methyl-3-(5-trifluoromethyl-1,3,4-thiadiazol-2-yl)ureido]propionaldehyde.

EXAMPLE 28

Preparation of
Tetrahydro-1-(5-trifluoromethyl-1,3,4-thiadiazol-2-yl)-3-methyl-6-hydroxy-2(1H)-pyrimidinone The dimethyl acetal of 3-[1-methyl-3-(5-trifluoromethyl-1,3,4-thiadiazol-2-yl)ureido]propionaldehyde (15 grams), water (400 ml) and hydrochloric acid (4 ml) are charged into a glass reaction vessel equipped with a mechanical stirrer, thermometer and reflux condenser. The reaction mixture is heated at reflux for a period of about 15 minutes. The reaction mixture is then filtered while hot and the filtrate is cooled resulting in the formation of a precipitate. The precipitate is recovered by filtration, is dried and is recrystallized to yield the desired product tetrahydro-1-(5-trifluoromethyl-1,3,4-thiadiazol-2-yl)-3-methyl-6-hydroxy-2(1H)-pyrimidinone.

EXAMPLE 29

Preparation of
Tetrahydro-1-(5-trifluoromethyl-1,3,4-thiadiazol-2-yl)-3-methyl-6-methoxy-2(1H)-pyrimidinone Tetrahydro-1-(5-trifluoromethyl-1,3,4-thiadiazol-2-yl)-3-methyl-6-hydroxy-2(1H)-pyrimidinone (7 grams), methyl alcohol (50 ml) and toluenesulfonic acid (0.2 grams) are charged into a glass reaction vessel equipped with a mechanical stirrer, thermometer and reflux heated The reaction mixture is then heated at reflux for a period of about 24 hours. After this time the mixture is stripped of unreacted alcohol under reduced pressure to yield a solid product. This product is then recrystallized to yield the desired product tetrahydro-1-(5-trifluoromethyl-1,3,4-thiadiazol-2-yl)-3-methyl-6-methoxy-2(1H)-pyrimidinone.

EXAMPLE 30

Preparation of 5-t-Butyl-1,3,4-thiadiazol-2-yl Isocyanate Dimer

A saturated solution of phosgene in ethyl acetate (100 ml) was charged into a glass reaction vessel equipped with a mechanical stirrer. A slurry of 5-t-butyl-2-amino-1,3,4-thiadiazole (10 grams) in ethyl acetate (300 ml) was added to the reaction vessel and the resulting mixture was stirred for a period of about 16 hours resulting in the formation of a precipitate. The reaction mixture was then purged with nitrogen gas to remove unreacted phosgene. The purged mixture was then filtered to recover the desired product 5-t-butyl-1,3,4-thiadiazol-2-yl isocyanate dimer as a solid having a melting point of 261° to 263°C.

EXAMPLE 31

Preparation of the Dimethyl Acetal of
3-[1-Methyl-3-(5-t-butyl-1,3,4-thiadiazol-2-yl)ureido]propionaldehyde A mixture of 5-t-butyl-1,3,4-thiadiazol-2-yl isocyanate dimer (6 grams), the dimethyl acetal of 3-methylaminopropionaldehyde (4.0 grams) and benzene (50 ml) are charged into a glass reaction flask equipped with a mechanical stirrer and reflux condenser. The reaction mixture is heated at reflux, with stirring, for a period of about 5 minutes. After this time the reaction mixture is stripped of benzene to yield a residue. The residue is then recrystallized to yield the desired product the dimethyl acetal of 3-[1-methyl-3-(5-t-butyl-1,3,4-thiadiazol-2-yl)ureido]propionaldehyde.

EXAMPLE 32

Preparation of Tetrahydro-1-(5-t-butyl-1,3,4-thiadiazol-2-yl)-3-methyl-6-hydroxy-2(1H)-pyrimidinone The dimethyl acetal of 3-[1-methyl-3-(5-t-butyl-1,3,4-thiadiazol-2-yl)ureido]propionaldehyde (16 grams), concentrated hydrochloric acid (10 ml) and water (500 ml) are charged into a glass reaction vessel equipped with a mechanical stirrer, thermometer and reflux condenser. The reaction mixture is heated at reflux for a period of about 15 minutes. The reaction mixture is filtered while hot and the filtrate is then cooled, resulting in the formation of a precipitate. The precipitate is recovered by filtration, dried and is recrystallized to yield the desired product tetrahydro-1-(5-t-butyl-1,3,4-thiadiazol-2-yl)-3-methyl-6-hydroxy-2(1H)-pyrimidinone.

EXAMPLE 33

Preparation of
Tetrahydro-1-(5-t-butyl-1,3,4-thiadiazol-2-yl)-3-methyl-6-methoxy-2(1H)-pyrimidinone Tetrahydro-1-(5-t-butyl-1,3,4-thiadiazol-2-yl)-3-methyl-6-hydroxy-2(1H)-pyrimidinone (7 grams), methyl alcohol (50 ml) and toluenesulfonic acid (0.2 grams) are charged into a glass reaction vessel equipped with a mechanical stirrer, thermometer and reflux condenser. The reaction mixture is then heated at reflux for a period of about 24 hours. After this time the mixture is stripped of unreacted alcohol under reduced pressure to yield a solid product. This product is then recrystallized to yield the desired product tetrahydro-1-(5-t-butyl-1,3,4-thiadiazol-2-yl)-3-methyl-6-methoxy-2(1H)-pyrimidinone.

EXAMPLE 34

Preparation of the Diethyl Acetal of
3-But-3-enylaminopropionaldehyde

But-3-enylamine (1.0 mole), the diethyl acetal of 3-bromopropionaldehyde (1.0 mole) and methanol (100 ml) are charged into a glass reaction vessel equipped with a mechanical stirrer, thermometer and reflux condenser. The reaction mixture is heated at reflux with stirring for a period of about 6 hours. After this time the reaction mixture is cooled to room temperature and sodium hydroxide (20 grams) is added. The reaction mixture is then stirred for an additional period of about 16 hours. The mixture is then filtered and the filtrate is distilled to yield the desired product the diethyl acetal of 3-but-3-enylaminopropionaldehyde.

EXAMPLE 35

Preparation of the Diethyl Acetal of
3-[1-But-3-enyl-3-(5-methoxy-1,3,4-thiadiazol-2-yl)ureido]propionaldehyde A mixture of 5-methoxy-1,3,4-thiadiazol-2-yl isocyanate dimer (0.05 mole), the diethyl acetal of 3-but-3-enylaminopropionaldehyde (0.1 mole) and benzene (60 ml) are charged into a glass reaction vessel equipped with a mechanical stirrer and reflux condenser. The reaction mixture is heated at reflux for a period of about 15 minutes. After this time the mixture is stripped of benzene under reduced pressure to yield the desired product the diethyl acetal of 3-[1-but-3-enyl-3-(5-methoxy-1,3,4-thiadiazol-2-yl)ureido]-propionaldehyde.

EXAMPLE 36

Preparation of Tetrahydro-1-(5-methoxy-1,3,4-thiadiazol-2-yl)-3-but-3-enyl-6-hydroxy-2(1H)-pyrimidinone The diethyl acetal of 3-[1-but-3-enyl-3-(5-methoxy-1,3,4-thiadiazol-2-yl)ureido]propionaldehyde (15 grams), water (400 ml) and hydrochloric acid (4 ml) are charged into a glass reaction vessel equipped with a mechanical stirrer, thermometer and reflux condenser. The reaction mixture is heated at reflux for a period of about 15 minutes. The reaction mixture is then filtered while hot and the filtrate is cooled to form a precipitate. The precipitate is recovered by filtration, is dried and is recrystallized to yield the desired product tetrahydro-1-(5-methoxy-1,3,4-thiadiazol-2-yl)-3-but-3-enyl-6-hydroxy-2(1H)-pyrimidinone.

EXAMPLE 37

Preparation of Tetrahydro-1-(5-methoxy-1,3,4-thiadiazol-2-yl)-3-but-3-enyl-6-ethoxy-2(1H)-pyrimidinone Tetrahydro-1-(5-methoxy-1,3,4-thiadiazol-2-yl)-3-but-3-enyl-6-hydroxy-2(1H)-pyrimidinone (7 grams), ethyl alcohol (50 ml) and toluenesulfonic acid (0.2 grams) are charged into a glass reaction vessel equipped with a mechanical stirrer, thermomater and reflux condenser. The reaction mixture is then heated at reflux for a period of about 24 hours. After this time the mixture is stripped of unreacted alcohol under reduced pressure to yield a solid product. This product is then recrystallized to yield the desired product tetrahydro-1-(5-methoxy-1,3,4-thiadiazol-2-yl)-3-but-3-enyl-6-ethoxy-2(1H)-pyrimidinone.

EXAMPLE 38

Preparation of the Diethyl Acetal of 3-(1,1-Dimethylprop-2-ynylamino)propionaldehyde 1,1-Dimethylprop-2-ynylamine (1.0 mole), the diethyl acetal of 3-bromopropionaldehyde (1.0 mole) and methanol (100 ml) are charged into a glass reaction vessel equipped with a mechanical stirrer, thermometer and reflux condenser. The reaction mixture is heated at reflux with stirring for a period of about 6 hours. After this time the reaction mixture is cooled to room temperature and sodium hydroxide (20 grams) is added. The reaction mixture is then stirred for an additional period of about 16 hours. The mixture is then filtered and the filtrate is distilled to yield the desired product the diethyl acetal of 3-(1,1-dimethylprop-2-ynylamino)propionaldehyde.

EXAMPLE 39

Preparation of the Diethyl Acetal of 3-[1-(1,1-Dimethylprop-2-ynyl)-3-(5-trifluoromethyl-1,3,4-thiadiazol-2-yl)ureido]propionaldehyde A mixture of 5-trifluoromethyl-1,3,4-thiadiazol-2-yl isocyanate dimer (0.05 mole), the diethyl acetal of 3-(1,1-dimethylprop-2-ynylamino)propionaldehyde (0.1 mole) and benzene (60 ml) are charged into a glass reaction vessel equipped with a mechanical stirrer and reflux condenser. The reaction mixture is heated at reflux for a period of about 15 minutes. After this time the mixture is stripped of benzene under reduced pressure to yield a solid product as the residue. The residue is then recrystallized to yield the desired product the diethyl acetal of 3-[1-(1,1-dimethylprop-2-ynyl)-3-(5-trifluoromethyl-1,3,4-thiadiazol-2-yl)ureido]propionaldehyde.

EXAMPLE 40

Preparation of Tetrahydro-1-(5-trifluoromethyl-1,3,4-thiadiazol-2-yl)-3-(1,1-dimethylprop-2-ynyl)-6-hydroxy-2(1H)-pyrimidinone The diethyl acetal of 3-[1-(1,1-dimethylprop-2-ynyl)-3-(5-trifluoromethyl-1,3,4-thiadiazol-2-yl)ureido]-propionaldehyde (15 grams), water (400 ml) and hydrochloric acid (4 ml) are charged into a glass reaction vessel equipped with a mechanical stirrer, thermometer and reflux condenser. The reaction mixture is heated at reflux for a period of about 15 minutes. The reaction mixture is then filtered while hot and the filtrate is cooled to form a precipitate. The precipitate is recovered by filtration, is dried and is recrystallized to yield the desired product tetrahydro-1-(5-trifluoromethyl-1,3,4-thiadiazol-2-yl)-3-(1,1-dimethylprop-2-ynyl)-6-hydroxy-2(1H)-pyrimidinone.

EXAMPLE 41

Preparation of Tetrahydro-1-(5-trifluoromethyl-1,3,4-thiadiazol-2-yl)-3-(1,1-dimethylprop-2-ynyl)-6-methoxy-2(1H)-pyrimidinone Tetrahydro-1-(5-trifluoromethyl-1,3,4-thiadiazol-2-yl)-3-(1,1-dimethylprop-2-ynyl)-6-hydroxy-2(1H)-pyrimidinone (7 grams), methyl alcohol (50 ml) and toluenesulfonic acid (0.2 grams) are charged into a glass reaction vessel equipped with a mechanical stirrer, thermometer and reflux condenser. The reaction mixture is then heated at reflux for a period of about 24 hours. After this time the mixture is stripped of unreacted alcohol under reduced pressure to yield a solid product. This product is then recrystallized to yield the desired product tetrahydro-1-(5-trifluoromethyl-1,3,4-thiadiazol-2-yl)-3-(1,1-dimethylprop-2-ynyl)-6-methoxy-2(1H)-pyrimidinone.

EXAMPLE 42

Preparation of 5-Allyl-1,3,4-thiadiazol-2-yl Isocyanate Dimer

A saturated solution of phosgene in ethyl acetate (100 ml) is charged into a glass reaction vessel equipped with a mechanical stirrer. A slurry of 5-allyl-2-amino-1,3,4-thiadiazole (40 grams) in ethyl acetate (300 ml) is added to the reaction vessel and the resulting mixture is stirred for a period of about 16 hours, resulting in the formation of a precipitate. The reaction mixture is then purged with nitrogen gas to remove unreacted phosgene. The purged mixture is then filtered to recover the precipitate. The precipitate is then recrystallized to yield the desired product 5-allyl-1,3,4-thiadiazol-2-yl isocyanate dimer.

EXAMPLE 43

Preparation of the Dimethyl Acetal of 3-Chloromethylaminopropionaldehyde

Chloromethylamine (1.0 mole), the dimethyl acetal of 3-bromopropionaldehyde (0.5 mole) and methanol (100 ml) are charged into a glass reaction vessel equipped with a mechanical stirrer, thermometer and reflux condenser. The reaction mixture is heated at reflux, with stirring, for a period of about 4 hours. After this time the reaction mixture is cooled to room temperature and sodium hydroxide (20 grams) is added. The reaction mixture is then stirred for an additional period of about 8 hours. The reaction mixture is then filtered and the filtrate is distilled under reduced pressure to yield the desired product the dimethyl acetal of 3-chloromethylaminopropionaldehyde.

EXAMPLE 44

Preparation of the Dimethyl Acetal of 3-[1-Chloromethyl-3-(5-allyl-1,3,4-thiadiazol-2-yl)ureido]propionaldehyde A mixture of 5-allyl-1,3,4-thiadiazol-2-yl isocyanate dimer (0.05 mole), the dimethyl acetal of 3-chloromethylamino-propionaldehyde (0.1 mole) and benzene (60 ml) are charged into a glass reaction vessel equipped with a mechanical stirrer and reflux condenser. The reaction mixture is heated at reflux for a period of about 15 minutes. After this time the mixture is stripped of benzene under reduced pressure to yield a solid product as the residue. The residue is then recrystallized to yield the desired product the dimethyl acetal of 3-[1-chloromethyl-3-(5-allyl-1,3,4-thiadiazol-2-yl)ureido]propionaldehyde.

EXAMPLE 45

Preparation of Tetrahydro-1-(5-allyl-1,3,4-thiadiazol-21yl)-3-chloromethyl-6-hydroxy-2(1H)-pyrimidinone The dimethyl acetal of 3-[1-chloromethyl-3-(5-allyl-1,3,4-thiadiazol-2-yl)ureido]propionaldehyde (15 grams), water (400 ml) and hydrochloric acid (4 ml) are charged into a glass reaction vessel equipped with a mechanical stirrer, thermometer and reflux condenser. The reaction mixture is heated at reflux for a period of about 15 minutes. The reaction mixture is then filtered while hot and the filtrate is cooled to form a precipitate. The precipitate is recovered by filtration, is dried and is recrystallized to yield the desired product tetrahydro-1-(5-allyl-1,3,4-thiadiazol-2-yl)-3-chloromethyl-6-hydroxy-2(1H)-pyrimidinone.

EXAMPLE 46

Preparation of Tetrahydro-1-(5-allyl-1,3,4-thiadiazol-2-yl)-3-chloromethyl-6-methoxy-2(1H)-pyrimidinone Tetrahydro-1-(5-allyl-1,3,4-thiadiazol-2-yl)-3-chloromethyl-6-hydroxy-2(1H)-pyrimidinone (7 grams), methyl alcohol (50 ml) and toluenesulfonic acid (0.2 grams) are charged into a glass reaction vessel equipped with a mechanical stirrer, thermometer and reflux condenser. The reaction mixture is then heated at reflux for a period of about 24 hours. After this time the mixture is stripped of unreacted alcohol under reduced pressure to yield a solid product. This product is then recrystallized to yield the desired product tetrahydro-1-(5-allyl-1,3,4-thiadiazol-2-yl)-3-chloromethyl-6-methoxy-2(1H)-pyrimidinone.

Additional exemplary compounds within the scope of the present invention which can be prepared by the procedures of the foregoing examples are tetrahydro-1-(5-ethyl-1,3,4-thiadiazol-2-yl)-3-butyl-6-pentyloxy-2(1H)-pyrimidinone, tetrahydro-1-(5-propyl-1,3,4-thiadiazol-2-yl)-3-pentyl-6-methoxy-2(1H)-pyrimidinone, tetrahydro-1-(5-isopropyl-1,3,4-thiadiazol-2-yl)-3-hexyl-6-methoxy-2(1H)-pyrimidinone, tetrahydro-1-(5-hexyl-1,3,4-thiadiazol-2-yl)-3-pent-3-enyl-6-methoxy-2(1H)-pyrimidinone, tetrahydro-1-(5-but-3-enyl-1,3,4-thiadiazol-2-yl)-3-hex-4-enyl-6-methoxy-2(1H)-pyrimidinone, tetrahydro-1-(5-hex-4-enyl-1,3,4-thiadiazol-2-yl)-3-bromomethyl-6-methoxy-2(1H)-pyrimidinone, tetrahydro-1-(5-chloromethyl-1,3,4-thiadiazol-2-yl)-3-$\beta$-bromoethyl-6-methoxy-2(1H)-pyrimidinone, tetrahydro-1-(5-$\beta$-bromoethyl-1,3,4-thiadiazol-2-yl)-3-$\gamma$-chloropropyl-6-methoxy-2(1H)-pyrimidinone, tetrahydro-1-(5-$\gamma$-chloropropyl-1,3,4-thiadiazol-2-yl)-3-$\omega$-chlorohexyl-6-methoxy-2(1H)-pyrimidinone, tetrahydro-1-(5-$\omega$-chlorohexyl-1,3,4-thiadiazol-2-yl)-3 -(1,1-diethylprop-2-ynyl)-6-methoxy-2(1H)-pyrimidinone, tetrahydro-1-(5-ethoxy-1,3,4-thiadiazol-2-yl)-3-(1-methyl-1-ethylprop-2-ynyl)-6-methoxy-2(1H)-pyrimidinone, tetrahydro-1-(5-propoxy-1,3,4-thiadiazol-2-yl)-3-(1,1-dipropylprop-2-ynyl)-6-methoxy-2(1H)-pyrimidinone, tetrahydro-1-(5-butyloxy-1,3,4-thiadiazol-2-yl)-3-methyl-6-methoxy-2(1H)-pyrimidinone, tetrahydro-1-(5-pentyloxy-1,3,4-thiadiazol-2-yl)-3-methyl-6-methoxy-2(1H)-pyrimidinone, tetrahydro-1-(5-ethylthio-1,3,4-thiadiazol-2-yl)-3-methyl-6-methoxy-2(1H)-pyrimidinone, tetrahydro-1-(5-propythio-1,3,4-thiadiazol-2-yl)-3-methyl-6-methoxy-2(1H)-pyrimidinone, tetrahydro-1-(5-butylthio-1,3,4-thiadiazol-2-yl)-3-methyl-6-methoxy-2(1H)-pyrimidinone, tetrahydro-1-(5-hexylthio-1,3,4-thiadiazol-2-yl)-3-methyl-6-methoxy-2(1H)-pyrimidinone, tetrahydro-1-(5-ethylsulfinyl-1,3,4-thiadiazol-2-yl)-3-methyl-6-methoxy-2(1H)-pyrimidinone, tetrahydro-1-(5-propylsulfinyl-1,3,4-thiadiazol-2-yl)-3-methyl-6-methoxy-2(1H)-pyrimidinone, tetrahydro-1-(5-hexylsulfinyl-1,3,4-thiadiazol-2-yl)-3-methyl-6-methoxy-2(1H)-pyrimidinone, tetrahydro-1 -(5-ethylsulfonyl-1,3,4-thiadiazol-2-yl)-3-methyl-6-methoxy-2(1H)-pyrimidinone, tetrahydro-1-(5-propylsulfonyl-1,3,4-thiadiazol-2-yl)-3-methyl-6-methoxy-2(1H)-pyrimidinone, tetrahydro-1-(5-hexylsulfonyl-1,3,4-thiadiazol-2-yl)-3-methyl-6-methoxy-2(1H)-pyrimidinone and the like.

For practical use as herbicides the compounds of this invention are generally incorporated into herbicidal compositions which comprise an inert carrier and a herbicidally toxic amount of such a compound. Such herbicidal compositions, which can also be called formulations, enable the active compound to be applied conveniently to the site of the weed infestation in any desired quantity. These compositions can be solids such as dusts, granules, or wettable powders; or they can be liquids such as solutions, aerosols, or emulsifiable concentrates.

For example, dusts can be prepared by grinding and blending the active compound with a solid inert carrier such as the talcs, clays, silicas, pyrophyllite, and the like. Granular formulations can be prepared by impregnating the compound, usually dissolved in a suitable solvent, onto and into granulated carriers such as the attapulgites or the vermiculities, usually of a particle size range of from about 0.3 to 1.5 mm. Wettable powders, which can be dispersed in water or oil to any desired concentration of the active compound, can be prepared by incorporating wetting agents into concentrated dust compositions.

In some cases the active compounds are sufficiently soluble in common organic solvents such as kerosene or xylene so that they can be used directly as solutions in these solvents. Frequently, solutions of herbicides can be dispersed under super-atmospheric pressure as aerosols. However, preferred liquid herbicidal compositions are emulsifiable concentrates, which comprise an active compound according to this invention and as the inert carrier, a solvent and an emulsifier. Such emulsifiable concentrates can be extended with water and/or oil to any desired concentration of active compound for application as sprays to the site of the weed infestation. The emulsifiers most commonly used in these concentrates are nonionic or mixtures of nonionic with anionic surface-active agents. With the use of some emulsifier systems an inverted emulsion (water in oil) can be prepared for direct application to weed infestations.

A typical herbicidal composition according to this invention is illustrated by the following example, in which the quantities are in parts by weight.

EXAMPLE 47

Preparation of a Dust

| Product of Example 5 | 10 |
| Powdered Talc | 90 |

The above ingredients are mixed in a mechanical grinder-blender and are ground until a homogeneous, free-flowing dust of the desired particle size is obtained. This dust is suitable for direct application to the site of the weed infestation.

The compounds of this invention can be applied as herbicides in any manner recognized by the art. One method for the control of weeds comprises contacting the locus of said weeds with a herbicidal composition comprising an inert carrier and as an essential active ingredient, in a quantity which is herbicidally toxic to said weeds, a compound of the present invention. The concentration of the new compounds of this invention in the herbicidal compositions will vary greatly with the type of formulation and the purpose for which it is designed, but generally the herbicidal compositions will comprise from about 0.05 to about 95 percent by weight of the active compounds of this invention. In a preferred embodiment of this invention, the herbicidal compositions will comprise from about 5 to about 75 percent by weight of the active compound. The compositions can also comprise such additional substances as other pesticides, such as insecticides, nematocides, fungicides, and the like; stabilizers, spreaders, deactivators, adhesives, stickers, fertilizers, activators, synergists, and the like.

The compounds of the present invention are also useful when combined with other herbicides and/or defoliants, dessicants, growth inhibitors, and the like in the herbicidal compositions heretofore described. These other materials can comprise from about 5 to about 95% of the active ingredients in the herbicidal compositions. Use of combinations of these other herbicides and/or defoliants, dessicants, etc. with the compounds of the present invention provide herbicidal compositions which are more effective in controlling weeds and often provide results unattainable with separate compositions of the individual herbicides. The other herbicides, defoliants, dessicants and plant growth inhibitors, with which the compounds of this invention can be used in the herbicidal compositions to control weeds, can include chlorophenoxy herbicides such as 2,4-D, 2,4,5-T, MCPA, MCPB, 4(2,4-DB), 2,4-DEB, 4-CPB, 4-CPA, 4-CPP, 2,4,5-TB, 2,4,5-TES, 3,4-DA, silvex and the like; carbamate herbicides such as IPC, CIPC, swep, barban, BCPC, CEPC, CPPC, and the like; thiocarbamate and dithiocarbamate herbicides such as CDEC, metham sodium, EPTC, diallate, PEBC, perbulate, vernolate and the like; substituted urea herbicides such as norea, siduron, dichloral urea, chloroxuron, cycluron, fenuron, monuron, monuron TCA, diuron, linuron, monolinuron, neburon, buturon, trimeturon and the like; symmetrical triazine herbicides such as simazine, chlorazine, atraone, desmetryne, norazine, ipazine, prometryn, atazine, trietazine, simetone, prometone, propazine, ametryne and the like; chloroacetamide herbicides such as 4-(chloroacetyl)morpholine, 1-(chloroacetyl)piperidine and the like; chlorinated aliphatic acid herbicides such as TCA, dalapon, 2,3-dichloropropionic acid, 2,2,3-TPA and the like; chlorinated benzoic acid and phenylacetic acid herbicides such as 2,3,6-TBA, 2,3,5,6-TBA, dicamba, tricamba, amiben, fenac, PBA, 2-methoxy-3,6-dichlorophenylacetic acid, 3-methoxy-2,6-dichlorophenylacetic acid, 2-methoxy-3,5,6-trichlorophenylacetic acid, 2,4-dichloro-3-nitrobenzoic acid and the like; and such compounds as aminotriazole, maleic hydrazide, phenyl mercuric acetate, endothal, biuret, technical chlordane, dimethyl 2,3,5,6-tetrachloroterephthalate, diquat, erbon, DNC, DNBP, dichlobenil, DPA, diphenamid, dipropalin, trifluralin, solan, dicryl, merphos, DMPA, DSMA, MSMA, potassium azide, acrolein, benefin, bensulide, AMS, bromacil, 2-(3,4-dichlorophenyl)-4-methyl-1,2,4-oxadiazolidine-3,5-dione, bromoxynil, cacodylic acid, CMA, CPMF, cypromid, DCB, DCPA, dichlone, diphenatril, DMTT, DNAP, EBEP, EXD, HCA, ioxynil, IPX, isocil, potassium cyanate, MAA, MAMA, MCPES, MCPP, MH, molinate, NPA, OCH, paraquat, PCP, picloram, DPA, PCA, pyrichlor, sesone, terbacil, terbutol, TCBA, brominil, CP-50144, H-176-1, H-732, M-2901, planavin, sodium tetraborate, calcium cyanamid, DEF, ethyl xanthogen disulfide, sindone, sindone B, propanil and the like.

Such herbicides can also be used in the methods and compositions of this invention in the form of their salts, esters, amides, and other derivatives whenever applicable to the particular parent compounds.

Weeds are undesirable plants growing where they are not wanted, having no economic value, and interfering with the production of cultivated crops, with the growing of ornamental plants, or with the welfare of livestock. Many types of weeds are known, including annuals such as pigweed, lambsquarters, foxtail, crabgrass, wild mustard, field pennycress, ryegrass, goose grass, chickweed, wild oats, velvet-leaf, purslane, barnyardgrass, smartweed, knotweed, cocklebur, wild buckwheat, kochia, medic, corn cockle, ragweed, sowthistle, coffeeweed, croton, cuphea, dodder, fumitory, groundsel, hemp nettle, knawel, spurge, spurry, emex, jungle rice, pondweed, dog fennel, carpetweed, morningglory, bedstraw, ducksalad, naiad, cheatgrass, fall panicum, jimsonweed, witchgrass, switchgrass, water-grass, teaweed, wild turnip and sprangletop; biennials such as wild carrot, matricaria, wild barley, campion, chamomile, burdock, mullein, roundleaved mallow, bull thistle, hounds-tongue, moth mullein and purple star thistle; or perennials such as white cockle, perennial ryegrass, quackgrass, Johnson grass, Canada thistle, hedge bindweed, Bermuda grass, sheep sorrel, curly dock, nutgrass, field chickweed, dandelion, campanula, field bindweed, Russian knapweed, mesquite, toadflax, yarrow, aster, gromwell, horsetail, ironweed, sesbania, bulrush, cattail, wintercress, horsenettle, nutsedge, milkweed and sicklepod.

Similarly, such weeds can be classified as broadleaf or grassy weeds. It is economically desirable to control the growth of such weeds without damaging beneficial plants or livestock.

The new compounds of this invention are particularly valuable for weed control because they are toxic to many species and groups of weeds while they are relatively nontoxic to many beneficial plants. The exact amount of compound required will depend on a variety of factors, including the hardiness of the particular weed species, weather, type of soil, method of application, the kind of beneficial plants in the same area, and the like. Thus, while the application of up to only about one or two ounces of active compound per acre may be sufficient for good control of a light infestation of weeds growing under adverse conditions, the application of 10 pounds or more of an active compound per acre may be required for good control of a dense infestation of hardy perennial weeds growing under favorable conditions.

The herbicidal toxicity of the new compounds of this invention can be demonstrated by the following established testing techniques known to the art, pre- and post-emergence testing.

The herbicidal activity of the compounds of this invention can be demonstrated by experiments carried out for the pre-emergence control of a variety of weeds. In these experiments small plastic greenhouse pots filled with dry soil are seeded with the various weed seeds. Twenty-four hours or less after seeding the pots are sprayed with water until the soil is wet and a test compound formulated as an aqueous emulsion of an acetone solution containing emulsifiers is sprayed at the desired concentrations on the surface of the soil.

After spraying, the soil containers are placed in the greenhouse and provided with supplementary heat as required and daily or more frequent watering. The plants are maintained under these conditions for a period of from 15 to 21 days, at which time the condition of the plants and the degree of injury to the plants is rated on a scale of from 0 to 10, as follows: 0 = no injury, 1,2 = slight injury, 3,4 = moderate injury, 5,6 = moderately severe injury, 7,8,9 = severe injury and 10 = death.

The herbicidal activity of the compounds of this invention can also be demonstrated by experiments carried out for the post-emergence control of a variety of weeds. In these experiments the compounds to be tested are formulated as aqueous emulsions and sprayed at the desired dosage on the foliage of the weeds that have attained a prescribed size. After spraying the plants are placed in a greenhouse and watered daily or more frequently. Water is not applied to the foliage of the treated plants. The severity of the injury is determined 10 to 15 days after treatment and is rated on the scale of from 0 to 10 heretofore described.

I claim:
1. A compound of the formula

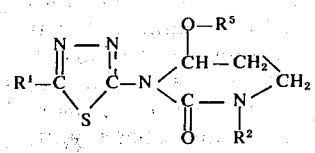

wherein $R^1$ is selected from the group consisting of lower alkyl, lower alkenyl, lower chloroalkyl, lower bromoalkyl, trifluoromethyl, lower alkoxy, lower alkylthio, lower alkylsulfonyl and lower alkylsulfinyl; $R^2$ is selected from the group consisting of lower alkyl, lower alkenyl, lower chloroalkyl, lower bromoalkyl, and

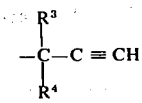

wherein $R^3$ and $R^4$ are each selected from the group consisting of hydrogen and lower alkyl; and $R^5$ is lower alkyl.

2. A compound of claim 1 which is, tetrahydro-1-(5-methyl-1,3,4-thiadiazol-2-yl)-3-methyl-6-methoxy-2(1H)-pyrimidinone.

3. A compound of claim 1 which is, tetrahydro-1-(5-methoxy-1,3,4-thiadiazol-2-yl)-3-ethyl-6-ethoxy-2(1H)-pyrimidinone.

4. A compound of claim 1 which is, tetrahydro-1-(5-methylthio-1,3,4-thiadiazol-2-yl)-3-propyl-6-propoxy-2(1H)-pyrimidinone.

5. A compound of claim 1 which is, tetrahydro-1-(5-methylsulfonyl-1,3,4-thiadiazol-2-yl)-3-allyl-6-butoxy-2(1H)-pyrimidinone.

6. A compound of claim 1 which is, tetrahydro-1-(5-methylsulfinyl-1,3,4-thiadiazol-2-yl)-3-propargyl-6-hexyloxy-2(1H)-pyrimidinone.

7. A compound of claim 1 which is, tetrahydro-1-(5-trifluoromethyl-1,3,4-thiadiazol-2-yl)-3-methyl-6-methoxy-2(1H)-pyrimidinone.

8. A compound of claim 1 which is, tetrahydro-1-(5-t-butyl-1,3,4-thiadiazol-2-yl)-3-methyl-6-methoxy-2(1H)-pyrimidinone.

* * * * *

UNITED STATES PATENT OFFICE
CERTIFICATE OF CORRECTION

PATENT NO. : 3,932,410
DATED : January 13, 1976
INVENTOR(S) : John Krenzer

It is certified that error appears in the above-identified patent and that said Letters Patent are hereby corrected as shown below:

The structure in column 1, lines 7 to 14, should appear as follows:

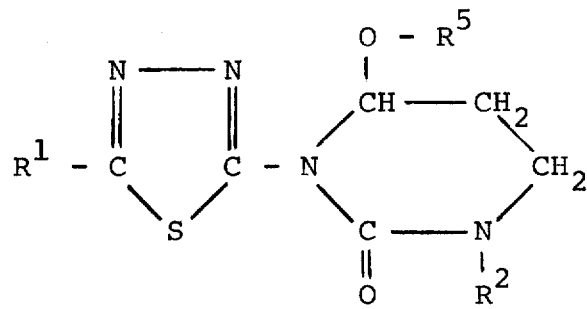

Signed and Sealed this

Twentieth Day of July 1976

[SEAL]

Attest:

RUTH C. MASON
Attesting Officer

C. MARSHALL DANN
Commissioner of Patents and Trademarks